United States Patent [19]

Domen et al.

[11] Patent Number: 5,142,027
[45] Date of Patent: Aug. 25, 1992

[54] CATIONIZED CARRIERS FOR IMMUNOGEN PRODUCTION

[75] Inventors: Patricia L. Domen; Greg Hermanson, both of Loves Park, Ill.

[73] Assignee: Pierce Chemical Company, Rockford, Ill.

[21] Appl. No.: 616,607

[22] Filed: Nov. 21, 1990

Related U.S. Application Data

[63] Continuation of Ser. No. 399,081, Aug. 28, 1989, abandoned.

[51] Int. Cl.⁵ .................... C07K 17/06; A61K 39/385
[52] U.S. Cl. ........................... 530/363; 530/362; 530/403; 530/404; 530/405; 530/406; 530/409; 424/88
[58] Field of Search ............... 530/363, 404, 405, 406, 530/362, 409, 403; 424/88

[56] References Cited

U.S. PATENT DOCUMENTS 4,384,995 5/1983 Stevens ........................... 530/403
4,769,237 9/1988 Bittle et al. ....................... 424/88

OTHER PUBLICATIONS

Chu et al (1982) J. Immunol. Methods 55: 73-78.
Border et al (1982) J. Clin. Invest. 69:451-461.
Pescer et al (1986) J. Immunol. Methods 87:21-27.

Primary Examiner—Christine Nucker
Assistant Examiner—Kay K. Kim

[57] ABSTRACT

A conjugate of a protein carrier and an antigen is disclosed. The carrier protein is cationized and the conjugate has enhanced immunogenic properties over those of the antigen alone. Cationization can be accomplished by derivatization of native carboxyl groups on the protein with an aklyl diamine, e.g. ethylene diamine, resulting in the formation of side chain aminoalkylamide groups, e.g. aminoethylamide.

4 Claims, 2 Drawing Sheets

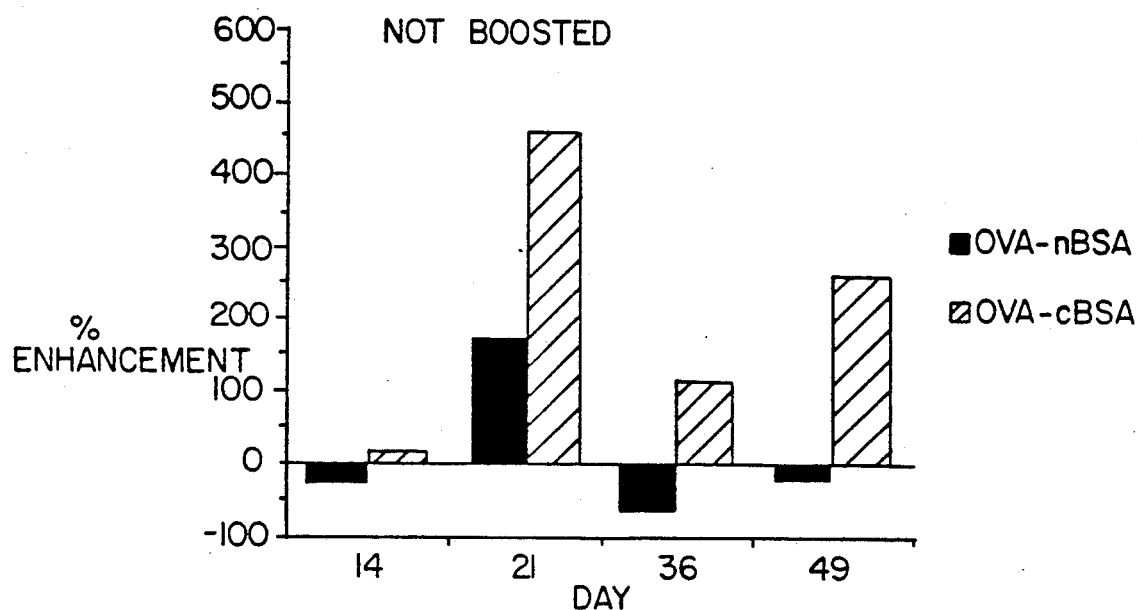
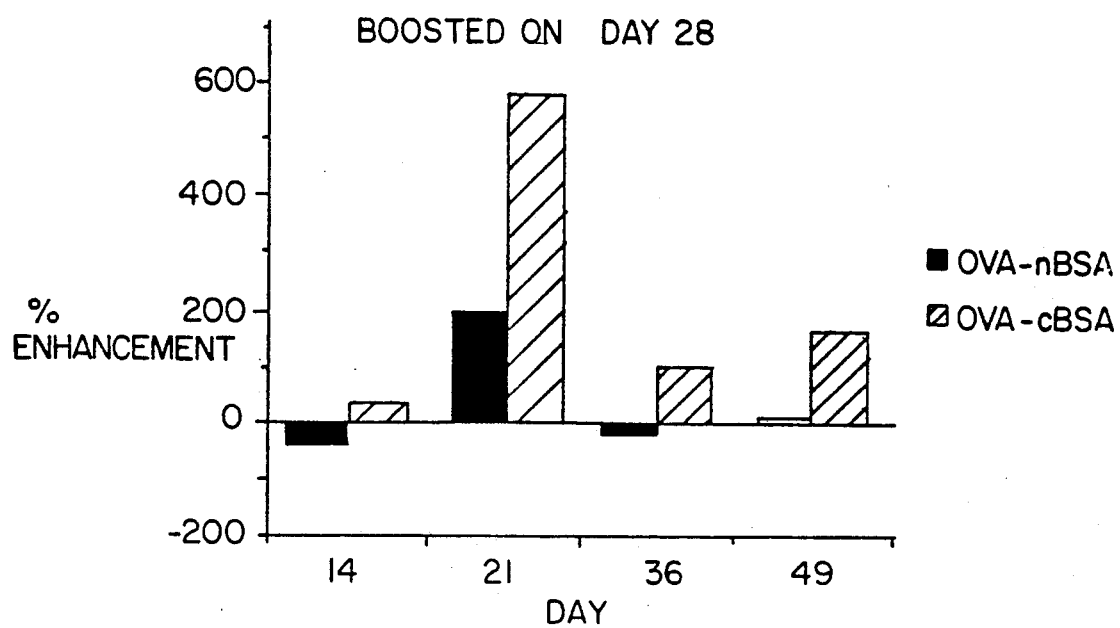

CATIONIZED CARRIERS FOR IMMUNOGEN PRODUCTION

RELATED APPLICATIONS

This application is a continuation of application Ser. No. 699,081, filed Aug. 28, 1989 now abandoned.

TECHNICAL FIELD

The present invention relates to the production of antibodies and more particularly, to conjugates which have enhanced ability to raise antibodies after injection into an animal.

BACKGROUND

Immunization protocols involve the injection of a substance capable of stimulating an immunogenic response into an animal and, after some period of time, bleeding the animal and recovering the antibodies so produced. The immunogenic substance, termed "an antigen," is generally dissolved or suspended in a matrix containing an adjuvant, such as Freund's Adjuvant, alum, etc., to enhance the immune response. Booster shots are also employed after the initial injection in order to enhance the response.

Even with the use of adjuvants and boosters, there are certain substances with potential antigenic characteristics which are simply too small to induce an antibody response when directly injected into an animal. Peptides, mycotoxins or other small molecules, termed "haptens," are examples of such substances. To utilize these as immunogenic substances, it is customary to conjugate, i.e. cross-link, them to a carrier protein such as bovine serum albumin (BSA) prior to injection. Coupling of the hapten to the protein is accomplished by reaction of the hapten with the functional groups of the protein.

As discussed by Chu, et al., in "Journal of Immunological Methods" 55 (1982) 73-78, the amount of hapten conjugated to each mole of carrier protein plays an important role in determining the quantity and specificity of the antibody response to the conjugate. In this instance, a large excess of mycotoxin was found to be necessary in the coupling reaction to yield a conjugate with the appropriate degree of substitution to function as a good antigen.

What Chu, et al., disclosed in the previously cited article is that modification of BSA with ethylene diamine gave an increase in the number of amino groups present on the carrier and thus enhanced the coupling efficiency of the hapten, mycotoxin. In turn, it is disclosed that the use of this resultant conjugate produces substantially higher antibody titers more rapidly than when the unmodified carrier conjugate was used.

Concerning substances which are themselves immunogenic without coupling to a carrier, e.g. BSA, researchers at the University of Cincinnati College of Medicine have published a series of papers reporting on how the response can be improved by cationizing the antigens prior to animal injection. The papers are as follows:

1. Muckerheide, et al., "The Journal of Immunology," 138, 833-837 (1987).
2. Muckerheide, et al., "The Journal of Immunology," 138, 2800-2804 (1987).
3. Domen, et al., "The Journal of Immunology," 139, 3295-3198 (1987).
4. Apple, et al., "The Journal of Immunology," 140, 3290-3295 (1988).

As illustrated in these articles, cationization of BSA is achieved by substituting native anionic side chain carboxyl groups with cationic amino ethylamide groups. As with Chu, this is achieved by reacting BSA with ethylenediamine.

While the articles in the "Journal of Immunology" identified above establish the fact that large molecule like BSA can be made an even more potent immunogen by cationization, to carry this concept over to other antigens may be time consuming and difficult. There are a number of proteins which the scientific community is interested in evaluating for immunogenic characteristics, and the protocol for cationizing each of them to achieve optimum enhancement is unique. In addition, direct cationization of some antigens may destroy or modify their native antigenic determinants, thus rendering them useless.

SUMMARY OF INVENTION

Having the foregoing in mind, the present invention provides a conjugate of a protein carrier and an antigen, said conjugate having enhanced immunogenic properties over those of the antigen alone. The carrier useful in the present invention is a protein which has been cationized. Preferably, cationization is accomplished by derivatization of native carboxyl groups on the protein with an alkyl diamine, e.g. ethylene diamine, resulting in the formation of side chain aminoalkylamide groups, e.g. aminoethylamide. Other amine containing compounds capable of introducing a positive charge on a protein can also be used so long as they do not sterically hinder conjugation to the antigen or adversely alter the antigenic character of the conjugate. As to the use of alkyldiamines, those having straight chain alkyl groups with 2-4 carbon atoms ar considered most useful.

A protein cationized as described above will have enhanced immunogenic properties over that of the native protein. The use of such a protein as a carrier in preparing immunogen conjugates results in a complex where the enhanced immunogen properties of the cationic carrier are transferred to the covalently coupled antigen, thereby producing a greater immune response toward the antigen.

A remarkable aspect of the present invention is that a cationized protein can be used as a carrier for large molecules immunogenic by themselves. This is a novel concept because, under normal circumstances, immunization with two immunogenic substances, either cross-linked or separate, produces only undesirable results. The second substance only serves to contaminate the system and potentially reduce the response to the first, and vice versa.

Therefore, there are distinct advantages to using a conjugate prepared in accordance with this invention. Immunization with the conjugate elicits an immune response to the antigen greater than that observed when the antigen is used alone. In many instances, the use of conjugates described in this invention may eliminate the need for booster immunizations. The enhanced immunogenicity of the cationized carrier is transferred to the antigen coupled to it without altering the native antigenic determinants of the antigen. The use of the cationized carrier eliminates the necessity for separately characterizing the optimum cationization protocol for each antigen, providing one exists.

Cationization of the protein carrier raises its isoelectric point and the extent of cationization should be such that when the protein is combined with the antigen of interest, the resulting conjugate has an isoelectric point (pI) greater than the antigen alone. Preferably the pI of the conjugate is about 7.5 to about 11. Great enhancement in immunogenicity is achieved with conjugates having a pI of 7.5 or more. Conjugates having a pI above about 11 may be toxic and, accordingly, would not ordinarily be useful. Cationized protein carriers having a pI of at least about 8 and less than about 12 have been found to be most useful.

Cationization of the protein carrier by forming the aminoalkylamide derivative thereof can be accomplished by known techniques such as illustrated in the above reference to Chu, et al., and the "Journal of Immunology" articles. In general, the carboxyl groups of the protein are activated by reaction with, for example, a water soluble carbodiimide followed by reaction with a diamine. Purification of the cationized protein is generally accomplished by dialysis against deionized water.

As with preparation of the cationized protein, conjugation thereof with an antigen of interest can be accomplished by known methods. The objective is to effectively conjugate antigen to the cationized carrier while minimizing the amount of polymerization so that the resulting conjugate is soluble at a physiological pH, i.e., about 7.5 As with the cationization reaction described above, conjugation can be accomplished using carbodiimide mediation for amide formation between the respective amino and carboxylic groups of the antigen and cationized protein. Alternatively, conjugation can be accomplished through the use of cross-linking reagents. These compounds usually have at least two reactive portions capable of covalently coupling to specific functional groups on proteins or other molecules. An illustration of this technique is described in Example VI where sulfo-SMCC (sulfosuccinimidyl 4-(N-maleimidomethyl) cyclohexane-1-carboxylate) is used to conjugate arginine vasopressin to cationized BSA (cBSA). In this case, one reactive portion of the cross-linker (the NHS-ester end) reacts with available primary amines on cBSA while the other reactive group (the maleimide end) is used to couple a peptide through its reduced sulfhydryl.

In addition to these compounds, alternate cross-linking reagents useful for this type of protein conjugation include dimethyl suberimidate (DMS), glutaraldehyde, and m-maleimidobenzoyl-N-hydroxysulosuccinimide ester (MBS). There are also many other similar cross-linkers which can be used to successfully conjugate a cationic carrier to an antigen. See Handbook and Gener Catalogue of Pierce Chemical Company, Rockford, Ill. (1989).

DESCRIPTION OF DRAWINGS

FIGS. 1A, 1B and 2 illustrate the immunogenic response in mice to the injection of various conjugated or unconjugated antigens.

DESCRIPTION OF PREFERRED EMBODIMENTS

Figure 2:
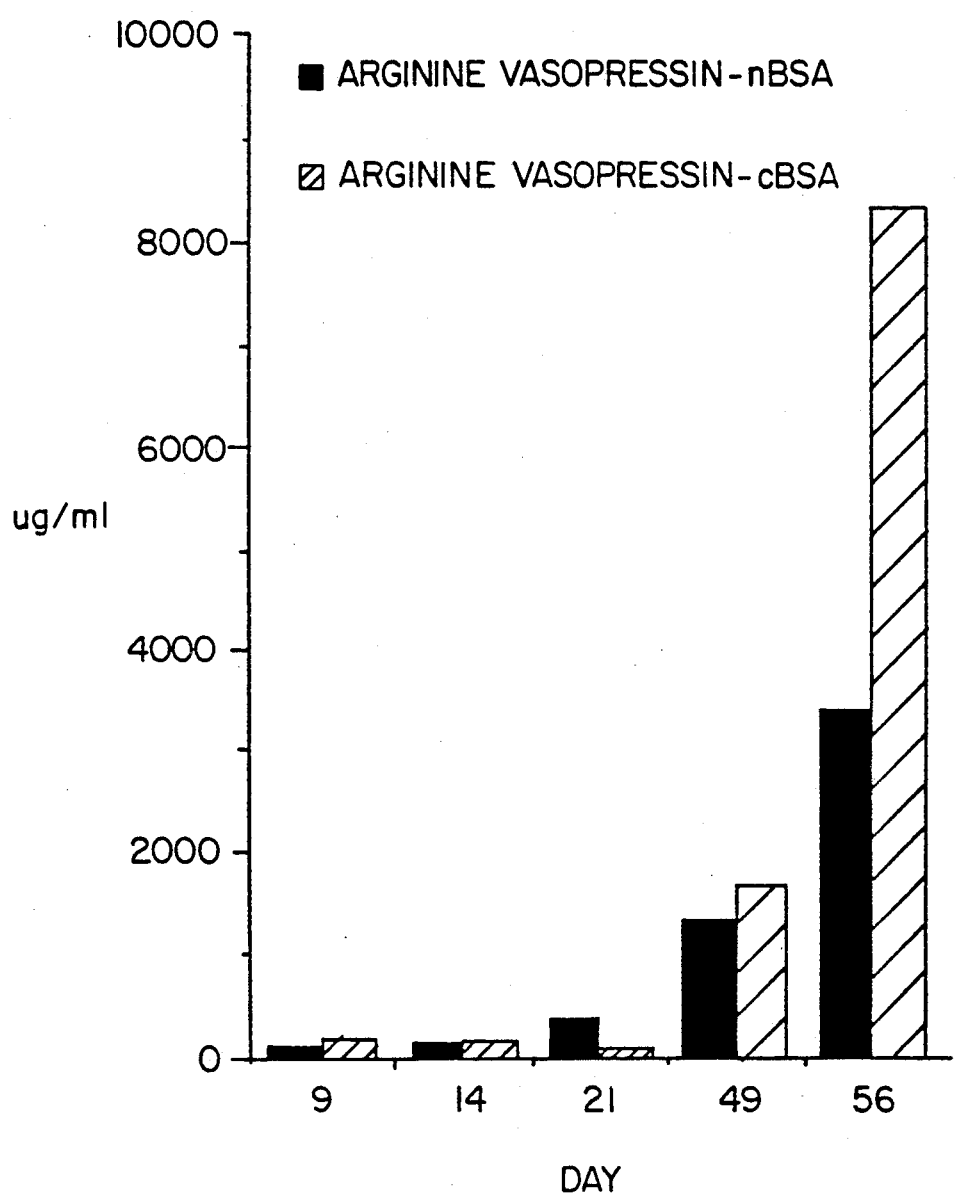

The following examples illustrate the present invention. All parts and percentages are by weight unless otherwise indicated.

EXAMPLE I

This example illustrates the protocol for the preparation of cationized bovine serum albumin (cBSA) which is useful as a cationized protein carrier.

1. 6.7 ml of ethylenediamine (EDA) was added to 50 ml of 0.1M MES (2-(N-morpholino) ethane sulfonic acid) buffer, pH 4.75. The pH was readjusted with concentrated HCl to pH 4.75 and cooled in an ice bath to ambient temperature (19°-24° C.) to prevent excess fuming.

2. Bovine serum albumin (500-mg) was dissolved in 2.5 ml of MES buffer (pH 4.75) and added to the above EDA solution.

3. Next, 180 mg of 1-ethyl-3-(3-dimethylaminopropyl) carbodiimide hydrochloride (EDC) was added with stirring.

4. The reaction was continued for 60 minutes at room temperature.

5. At the end of 1 hour, the reaction was quenched with 3 ml of 4M sodium acetate, pH 4.75.

6. The solution was then dialyzed exhaustively against D.I. water (4 days, 5 changes, 20 liters each) to remove excess reagents.

7. The salt-free preparation of cBSA was finally lyophilized and stored at 4° C.

The degree of cationization, in terms of pI, of the protein carrier prepared above is determined by isoelectric focusing using the following procedure:

1. The mold for a LKB Multiphor system was prepared as described in the instruction manual.

2. A commercially available (Amresco) mixture of acrylamide (30%) and N,N'methylenebisacrylamide (1%) was used as a stock solution. The gel was prepared as follows:

| | |
|---|---|
| Acrylamide/Bis | 20 ml |
| Glycerol (87% v/v) | 7 ml |
| LKB ampholine pH 9-11 | 3 ml |
| Distilled water | 30 ml |
| De-gas for 10 minutes. | |
| Ammonium persulphate (1% w/v) | 2 ml |
| Mix by swirling. | |
| Fill the mold completely. | |
| Allow gel to polymerize. | |

3. A template was placed on the cooling plate of the Multiphor with a thin film of Tween 20 in between. The mold was dismantled and the gel on the 1 mm supporting plate was placed on the template with a thin film of Tween 20 in between.

4. The electrode strips were soaked with 1M NaOH (cathode) or 1M $H_3PO_4$ (anode) and applied to the gel surface.

5. Pieces of filter paper were evenly spaced on the gel, using the template as a guide, about 1 cm from the anode. The samples were applied in 15 ul aliquots at a concentration of 6 mg/ml.

6. The electrode holder and lid were positioned and the unit connected to a power supply. The gel was run at 25 W constant power, at 10° C., with 63 mA of current (initial setting) and 1360 volts (final reading) for 70 minutes.

7. The lid and electrode holder were removed. The sample application strips were removed with forceps. The pH of the gel was measured at 1 cm intervals using a surface electrode (Orion) and a standard curve was generated.

8. The apparatus was reassembled and the gel was refocused for 10 minutes.

9. The unit was disassembled and the gel on the supporting glass plate was placed in fixing solution (50% ethanol and 5% acetic acid) for 30 minutes.

10. The gel was transferred into destaining solution (10% ethanol and 10% acetic acid) for 5 minutes.

11. The gel was stained in Coomassie Blue staining solution for 10 minutes.

12. The gel was destained overnight.

13. The migration distance for each protein was measured and pI determined by reading from the standard curve.

The pI of the cationized protein carrier prepared in Example I was 7.7–9.7.

EXAMPLE II

This example illustrates the protocol for preparing a conjugate of a high molecular weight antigen (ovalbumin) and a cationized protein carrier.

1. Dissolve 6 mg of cBSA, prepared as described in Example I, 6 mg of ovalbumin, and 2.5 mg EDC in 3 ml of MES buffer, pH 4.75.

2. Stir the reaction for 60 minutes at room temperature.

3. The reaction mixture now containing the conjugate of ovalbumin (OVA) and cBSA was then quenched with 35 ul of 4M sodium acetate, pH 4.75, per ml of conjugate solution.

4. The conjugate was desalted by dialysis against PBS, pH 7.4 (0.01M sodium phosphate, 0.15 M NaCl).

5. The dialyzed solution was lyophilized and stored at 4° C.

The pI of the conjugate prepared in this Example was 7.9–8.6, as determined by the procedure set forth in Example I.

EXAMPLE III

This Example describes the use of the conjugate prepared in Example II, as well as the use of other antigens. The antigens used were (a) the OVA-cBSA conjugate prepared in Example II, (b) an OVA-native bovine serum albumin conjugate (OVA-nBSA) prepared by the basic protocol set forth in Example II using nBSA rather than cBSA, and (c) just OVA. To standardize for the amount of antigen injected, 20 micrograms of OVA were injected and 40 micrograms of each conjugate.

Mice were immunized by intraperitoneal (i.p.) injection of antigen mixed with an equal volume of alum (2.25 mg) as adjuvant. On day 28, half of the animals received a boost identical to the primary immunization. The immunized mice were bled periodically through the retro orbital plexus. The specific antibody response, expressed as percent of enhancement compared to the response to unconjugated OVA was determined by an enzyme linked immunosorbant assay (ELISA). Ferguson, T. A., T. Peters, Jr., R. Reed, A. J. Pesce and J. G. Michael. 1983. Immunoregulatory properties of antigenic fragments from bovine serum albumin. Cell. Immunol. 78:1–12.

The results of immunization with the antigens identified in this Example are illustrated in FIG. 1. As shown in FIG. 1A, the use of the conjugate of the present invention (OVA-cBSA) for primary immunization results in a substantially greater production of antibody than either OVA alone or the conjugate, OVA-nBSA.

The anti-OVA response in mice immunized with the OVA-cBSA conjugate is enhanced by 100% (day 36) and 250% (day 49) the response of animals immunized with OVA alone. In contrast, rather than being enhanced, the anti-OVA response in mice immunized with the non-cationized OVA-nBSA conjugate is actually slightly lower at times than the response to OVA alone. As seen in FIG. 1B, the pattern of enhancement with the cationized carrier is maintained following a boost. The results shown in FIG. 1 indicate that covalently coupling an antigen to a cationized protein carrier produces an enhanced immune response toward the antigen.

EXAMPLES IV and V

Example III was repeated except that the antigens Human IgG (Examples IV) and Fetuin (Example V) were used in place of OVA. The conjugates of these antigens with cBSA had pI's of 7.85–8.92 and 7.88–8.17, respectively. As with the conjugate of Example III the conjugates of these Examples yielded an enhanced immune response compared with the antigen alone.

The foregoing Examples demonstrate that a conjugate of a cationized protein carrier and antigen produces an enhanced immune response toward the antigen. The same phenomena is observed when a cationized protein is coupled to a hapten which by itself is not immunogenic because of its small size. As indicated previously, with haptens, it is necessary to couple them to a larger carrier molecule such as a protein to elicit an immunogenic response. As opposed to antigens which have a molecular weight of about 5,000 and above, haptens have a molecular weight of less than about 5,000. Molecular weight can be determined by polyacrylamide gel electrophoresis using known molecular weight standards as markers.

Thus, in accordance with a further aspect of the present invention, a conjugate of a cationized protein carrier and a hapten is provided By using a cationized protein carrier to form the conjugate with the hapten, an enhanced immunogenic response to the hapten can be obtained, compared to the response obtained using the non-cationized form of the protein as the carrier. This phenomena is illustrated in the following Example VI.

EXAMPLE VI

This Example illustrates the preparation of a conjugate of a hapten, the peptide arginine vasopressin, and the protein carrier of Example I.

For coupling the peptide to the carrier, the peptide was first activated by reaction with sulfo-SMCC (sulfosuccinimidyl 4-(N-maleimidomethyl) cyclohexane-1-carboxylate). The compound is a cross-linker which has an NHS-ester for amine coupling to the carrier protein and a terminal maleimide group for coupling to sulfhydryl groups of peptides.

Arginine vasopressin is a representative peptide that is a readily available, naturally occurring, disulfide containing molecule. The disulfide groups of the peptide were reduced with an immobilized reductant prior to conjugating to the cBSA or nBSA. The protocol for preparation of the conjugates is as follows:

A. Activation of cBSA and nBSA with Sulfo-SMCC:

1. 20 mg of nBSA (Pentex Grade, 5 times recrystallized, Miles Laboratories, Inc.) and cBSA (prepared as in Example I) were dissolved in 1.0 ml of 10 mM sodium phosphate, pH 7.0 in separate test tubes.

2. The solutions were added to separate tubes containing 5.0 mg sulfo-SMCC and vortex mixed until dissolved. The solution containing cBSA appeared hazy while the nBSA solution remained clear.

3. The reactions were allowed to continue for 1 hour at room temperature.

4. Two 15 ml desalting columns containing acrylamide gel (exclusion limit M.W. 5000) were equilibrated with 0.1M ammonium bicarbonate, pH 6.0.

5. The maleimide-activated proteins were applied to the columns and eluted using the same buffer while taking 2 ml fractions. Those fractions containing protein (*) were pooled and freeze-dried.

| Fraction | cBSA | nBSA |
|---|---|---|
| 1 | .003 | .036 |
| 2 | .004 | .021 |
| 3 | .076 | *2.867 |
| 4 | *> | *> |
| 5 | .944 | .780 |
| 6 | 2.217 | > |

B. Coupling of Arginine Vasopressin to Maleimide-Activated Proteins:

1. 5 mg of arginine vasopressin (AV;Sigma) was dissolved in 1.25 ml of PBS, pH 7.6, making a 4 mg/ml solution.

2. 1.0 ml of the above AV solution was applied to a 2.0 ml immobilized lipoic acid column to reduce the disulfides of the peptide.

3. 3 mg of lyophilized sulfo-SMCC activated proteins (both cBSA and nBSA) were dissolved in 1 ml of the immobilized lipoic acid column eluate which contained the reduced arginine vasopressin.

4. Conjugation was carried out with overnight incubation at room temperature without stirring.

5. Unconjugated peptide was removed by desalting using a 15 ml desalting column equilibrated with PBS, pH 7.0 (without azide).

6. Fractions containing protein were pooled and freeze-dried.

EXAMPLE VII

Mice were immunized and bled as described in Example III. With the peptide, however, 100 micrograms of conjugate were used. After a 49 day bleed, the mice were boosted with an immunization identical to the first.

The antibody response was determined as described in Example III with the response being expressed as a $\mu g/ml$. The response to the arginine vasopressin conjugates is shown in FIG. 2. The early response to both the cBSA and nBSA conjugates is similar. After the boost, however, there is a two-fold enhancement with the cationized carrier.

In addition to peptide conjugates, the immune response of other carrier-hapten conjugates can be enhanced by using cationized protein as the carrier. Examples include conjugates of cationized protein and the following haptens: lipids, carbohydrates, nucleic acids and mycotoxins.

While this invention has been described and illustrated with respect to certain preferred embodiments thereof, it is not to be limited to those embodiments. Rather, the invention is as described in the appended claims

We claim:

1. A physiologically soluble conjugate of a carrier and an antigen, said antigen having a molecular weight of 5,000 or more and which itself can elicit an immune response, said carrier being a cationized protein and said conjugate eliciting an immune response to said antigen which is greater than that to the antigen alone.

2. The conjugate of claim 1 wherein the cationized protein has an isoelectric point above about 8.

3. The conjugate of claim 2 wherein the carrier is cationized serum albumin, said cationization being achieved by formation of aminoalkyl amide groups.

4. The conjugate of claim 3 having a pI of 7.5-11 wherein the carrier is cationized bovine serum albumin and said aminoalkyl amide groups are aminoethyl amide groups.

* * * * *